(12) United States Patent
Jiang et al.

(10) Patent No.: US 11,904,138 B2
(45) Date of Patent: Feb. 20, 2024

(54) GLUCOSE LEVEL MANAGEMENT WITHOUT CARBOHYDRATE COUNTING

(71) Applicant: Medtronic MiniMed, Inc., Northridge, CA (US)

(72) Inventors: Boyi Jiang, Pasadena, CA (US); Yuxiang Zhong, Arcadia, CA (US); Pratik J. Agrawal, Porter Ranch, CA (US); Ali Dianaty, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 427 days.

(21) Appl. No.: 17/162,042

(22) Filed: Jan. 29, 2021

(65) Prior Publication Data
US 2022/0241500 A1    Aug. 4, 2022

(51) Int. Cl.
| | |
|---|---|
| *A61M 5/172* | (2006.01) |
| *G16H 50/20* | (2018.01) |
| *G16H 20/60* | (2018.01) |
| *A61K 9/00* | (2006.01) |
| *A61K 38/28* | (2006.01) |

(52) U.S. Cl.
CPC ......... *A61M 5/1723* (2013.01); *A61K 9/0009* (2013.01); *A61K 9/0019* (2013.01); *A61K 38/28* (2013.01); *G16H 20/60* (2018.01); *G16H 50/20* (2018.01); *A61M 2205/52* (2013.01); *A61M 2230/201* (2013.01)

(58) Field of Classification Search
CPC ............ A61M 5/1723; A61M 5/14244; A61M 5/14248; A61B 5/14532; A61B 5/4839; G16H 20/17; G16H 50/50; G16H 40/63
See application file for complete search history.

(56) References Cited

U.S. PATENT DOCUMENTS

| | | | | |
|---|---|---|---|---|
| 8,924,160 | B2* | 12/2014 | Moerman | A61P 3/10 703/11 |
| 2009/0164190 | A1* | 6/2009 | Hayter | G16H 50/50 703/11 |
| 2011/0098548 | A1* | 4/2011 | Budiman | G16Z 99/00 600/365 |
| 2018/0169332 | A1 | 6/2018 | Sadeghzadeh et al. | |
| 2019/0246914 | A1* | 8/2019 | Constantin | A61B 5/1118 |

(Continued)

OTHER PUBLICATIONS

Extended Search Report from counterpart European Application No. 22153634.5 dated Jun. 21, 2022, 12 pp.

(Continued)

*Primary Examiner* — Manuel A Mendez
(74) *Attorney, Agent, or Firm* — Weaver Austin Villeneuve & Sampson LLP

(57) ABSTRACT

Disclosed herein are techniques related to glucose level management without carbohydrate counting. The techniques may involve obtaining contextual information for a meal, predicting amounts of glucose to be absorbed into a bloodstream of the patient over a duration of time due to consumption of the meal based on the contextual information for the meal, determining one or more amounts of insulin to counteract effects of the predicted amounts of glucose, and affecting insulin therapy based on outputting information indicative of the determined one or more amounts of insulin.

20 Claims, 9 Drawing Sheets

(56) References Cited

U.S. PATENT DOCUMENTS

2020/0135320 A1    4/2020    Vleugels
2022/0241501 A1    8/2022    Jiang et al.

OTHER PUBLICATIONS

U.S. Non-Final Office Action dated Jun. 1, 2023 in U.S. Appl. No. 17/162,065.
U.S. Restriction Requirement dated Mar. 1, 2023 in U.S. Appl. No. 17/162,065.
Brazeau et al., "Carbohydrate counting accuracy and blood glucose variability in adults with type 1 diabetes," Diabetes Research and Clinical Practice, vol. 99, No. 1, Jan. 2013, 5 pp.
IEEE 802.11ad, "IEEE Standard for Information Technology—Telecommunications and Information Exchange Between Systems—Local and Metropolitan Area Networks—Specific Requirements—Part 11: Wireless LAN Medium Access Control (MAC) and Physical Layer (PHY) Specifications—Amendment 3: Enhancements for Very High Throughput in the 60 GHz Band", IEEE Computer Society, Dec. 28, 2012, 628 pp.
Jiang, B., "Estimating an Optimal Meal Bolus for Person with Diabetes on Multiple Daily Injections Therapy without Carb Counting," American Diabetes Association 80th Scientific Sessions, Jun. 12-16, 2020, 9 pp.
Reiterer et al., "Impact of Carbohydrate Counting Errors on Glycemic Control in Type 1 Diabetes, " IFAC—PapersOnLine, vol. 51, No. 27, Dec. 2018, 6 pp.

\* cited by examiner

US 11,904,138 B2

GLUCOSE LEVEL MANAGEMENT WITHOUT CARBOHYDRATE COUNTING

TECHNICAL FIELD

The disclosure relates to medical systems and, more particularly, to medical systems for therapy for diabetes.

BACKGROUND

A patient with diabetes typically receives insulin from an insulin delivery device (e.g., a pump or injection device) to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include basal dosages and bolus dosages of insulin. Basal dosages tend to keep blood glucose levels at consistent levels during periods of fasting. Bolus dosages may be delivered to a patient specifically at or near mealtimes or other times where there may be a relatively fast change in glucose level.

SUMMARY

Disclosed herein are techniques related to glucose level management without carbohydrate counting. The techniques may be practiced using systems; processor-implemented methods; and non-transitory processor-readable storage media storing instructions which, when executed by one or more processors, cause performance of the techniques.

In some examples, the techniques involve obtaining contextual information for a meal, predicting amounts of glucose to be absorbed into a bloodstream of the patient over a duration of time due to consumption of the meal based on the contextual information for the meal, determining one or more amounts of insulin to counteract effects of the predicted amounts of glucose, and affecting insulin therapy based on outputting information indicative of the determined one or more amounts of insulin.

In some examples, the techniques may involve obtaining contextual information for a meal, utilizing a machine learning technique to determine, based on the contextual information for the meal, a dosage of insulin that corresponds to a maximum amount of time within a target range for a patient's glucose levels, and affecting insulin therapy of the patient based on outputting information indicative of the determined dosage.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
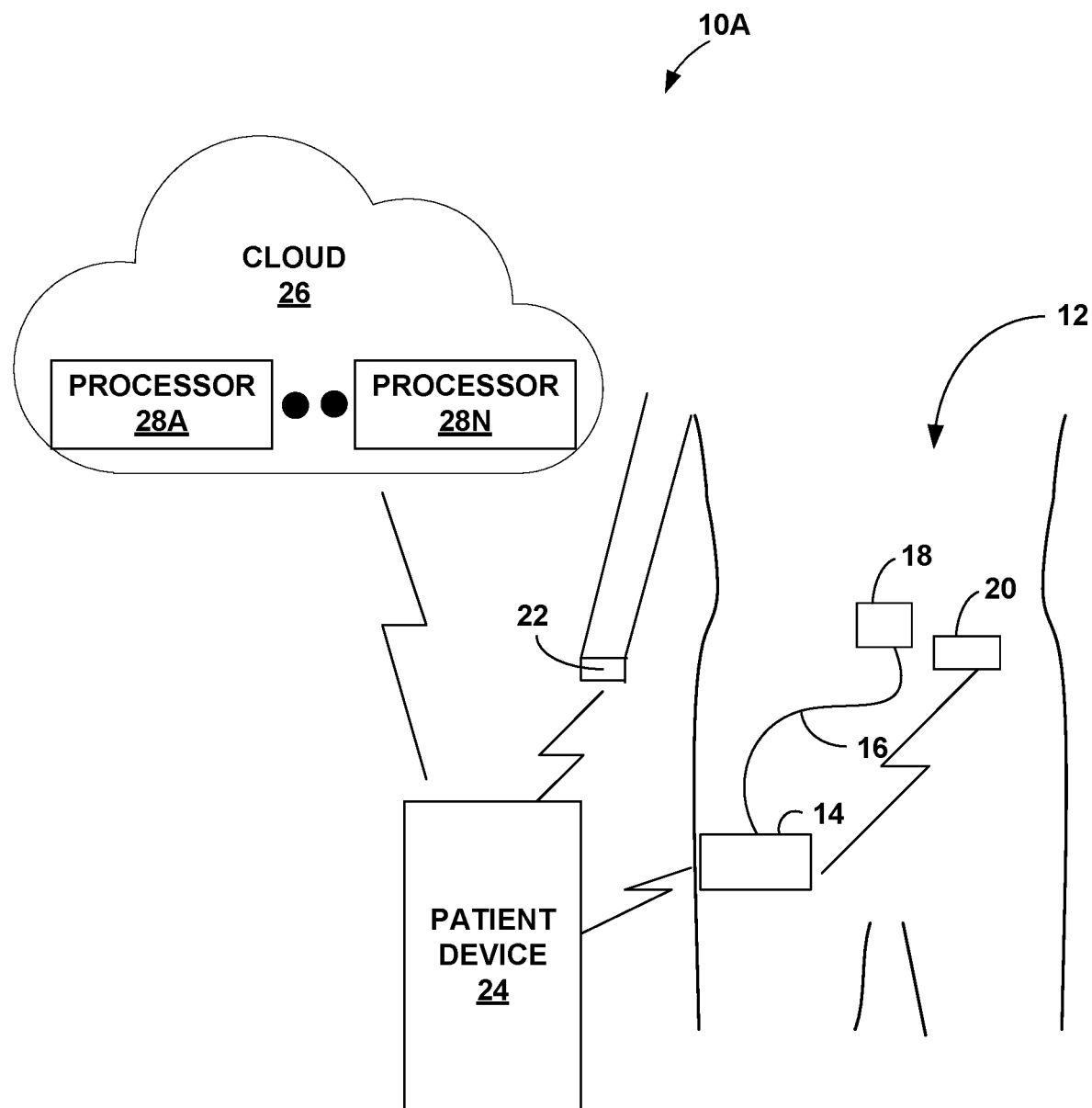
FIG. 1 is a block diagram illustrating an example glucose level management system comprising an insulin pump, in accordance with one or more examples described in this disclosure.

Devices, systems, and techniques for managing glucose levels in a patient are described in this disclosure. For diabetics, consumption of carbohydrates can increase glucose levels to higher levels than for non-diabetics because diabetics tend to be resistant to insulin or fail to produce sufficient insulin to counteract the effects of the carbohydrates. To keep the glucose levels within a desired range (e.g., a predetermined target range having an upper limit that is a predetermined number of values below a hyperglycemic glucose level and a lower limit that is a predetermined number of values above a hypoglycemic glucose level), diabetic patients typically receive insulin from an external source (e.g., insulin pump or by injection) to keep the glucose levels within the desired range. Because the amount of carbohydrates a patient consumes may impact the glucose level of the patient, the amount of insulin that is to be delivered may be based on the amount of carbohydrates that patient consumes.

One way in which to determine the amount of carbohydrates the patient is to consume/is consuming/did consume is to rely on carbohydrate counting. For example, before, during, or immediately after a meal, a computing device may receive user input that indicates the amount of carbohydrates the patient will consume/is consuming/did consume. However, relying on the patient to enter the amount of carbohydrates can be cumbersome to the patient, and the patient may fail to reliably enter the amount of carbohydrates. Moreover, even if the patient does enter the amount of carbohydrates, there is the possibility that the entry is inaccurate (e.g., the patient consumed more or fewer carbohydrates than entered). Accordingly, relying solely on patient entry of the amount of carbohydrates may result in inaccurate determination of the amount of insulin the patient is to receive.

To avoid the shortcomings related to carbohydrate counting, the techniques disclosed herein enable glucose level management without carbohydrate counting. Advantageously, by avoiding carbohydrate counting, such techniques may reduce the burden on the patient, as well as potentially provide for a more accurate determination of the amount of insulin to be delivered to the patient.

In some examples, carbohydrate counting may be avoided through the use of artificial intelligence techniques (e.g., statistical averaging techniques, pattern matching techniques, and/or machine learning techniques). For example, in some carbohydrate counting schemes, an amount of carbohydrates may be provided as input to a physiological model of a patient. The physiological model may be used to determine an "impact on blood glucose" of the amount of carbohydrates provided as input. The impact on blood glucose may be represented as a time series of blood glucose levels like the one depicted in FIG. 7. Thus, to avoid carbohydrate counting, artificial intelligence techniques may be used to predict the impact on blood glucose based on contextual information (e.g., time of day, day of week, and/or geolocation) instead of user input indicative of an amount of carbohydrates. For example, the impact on blood glucose of a weekend dinner at the patient's favorite steakhouse may be predicted based on one or more similar meals.

Additionally or alternatively, artificial intelligence techniques may be used to determine an insulin dosage based on contextual information. For example, genetic programming may be used to determine an insulin dosage for counteracting a predicted impact on blood glucose such that time-in-range is maximized for the patient.

It should be appreciated that the techniques disclosed herein can be practiced with one or more types of insulin (e.g., fast-acting insulin, intermediate-acting insulin, and/or slow-acting insulin). Thus, terms such as "basal insulin" and "bolus insulin" do not necessarily denote different types of insulin. For example, fast-acting insulin may be used for both basal dosages and bolus dosages.

FIG. 1 is a block diagram illustrating an example glucose level management system, in accordance with one or more examples described in this disclosure. FIG. 1 illustrates system 10A that includes insulin pump 14, tubing 16, infusion set 18, monitoring device 20 (e.g., a glucose level monitoring device), wearable device 22, patient device 24, and cloud 26. Cloud 26 represents a local, wide area or global computing network including one or more processors 28A-28N ("one or more processors 28") that are within one or more network devices (e.g., one network device may include one or more processors 28 or one or more processors 28 may be distributed across a plurality of network devices). In some examples, the various components may determine changes to therapy based on determination of glucose level by monitoring device 20, and therefore system 10A may be referred to as glucose level management system 10A.

Patient 12 may be diabetic (e.g., Type 1 diabetic or Type 2 diabetic), and therefore, the glucose level in patient 12 may be controlled with delivery of supplemental insulin. For example, patient 12 may not produce sufficient insulin to control the glucose level, or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Monitoring device 20 may also be coupled to patient 12 to measure glucose level in patient 12. Insulin pump 14, tubing 16, infusion set 18, and monitoring device 20 may together form an insulin pump system. One example of the insulin pump system is the MINIMED™ 670G insulin pump system by MEDTRONIC MINIMED, INC. However, other examples of insulin pump systems may be used and the example techniques should not be considered limited to the MINIMED™ 670G insulin pump system. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or monitoring device 20 may be contained in the same housing.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places, and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery-powered device that is powered by replaceable and/or rechargeable batteries.

Tubing 16 may connect at a first end to a reservoir in insulin pump 14 and may connect at a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern of tubing 16 breaking.

Infusion set 18 may include a thin cannula that patient 12 inserts into a layer of fat under the skin (e.g., subcutaneous connection). Infusion set 18 may rest near the stomach of patient 12. The insulin may travel from the reservoir of insulin pump 14, through tubing 16, through the cannula in infusion set 18, and into patient 12. In some examples, patient 12 may utilize an infusion set insertion device. Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

In some examples, insulin pump 14 may be an implantable insulin pump. For ease of description, the disclosure is described with respect to insulin pump 14 being external to patient 12.

Monitoring device 20 may include a sensor that is inserted under the skin of patient 12, such as near the stomach of patient 12 or in the arm of patient 12 (e.g., subcutaneous connection). Monitoring device 20 may be configured to measure the interstitial glucose level, which is the glucose found in the fluid between the cells of patient 12. Monitoring device 20 may be configured to continuously or periodically sample the glucose level and rate of change of the glucose level over time.

In one or more examples, insulin pump 14, monitoring device 20, and/or the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from monitoring device 20 and, in response, may increase or decrease the amount of insulin delivered to patient 12 (e.g., by delivering a varying number of discrete boluses of insulin or changing the bolus size of insulin). For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

Insulin pump 14 and monitoring device 20 may be configured to operate together to mimic some of the ways in which a healthy pancreas works. Insulin pump 14 may be configured to deliver basal dosages, which is a small amount of insulin released continuously or substantially continuously throughout the day. There may be times when glucose levels increase, such as due to eating or some other activity that patient 12 undertakes. Insulin pump 14 may be configured to deliver bolus dosages on demand in association with food intake or to correct an undesirably high glucose level in the bloodstream, e.g., supplementing the basal insulin delivery. In one or more examples, if the glucose level rises above a target level, then insulin pump 14 may deliver a bolus dosage to address the increase in glucose level. Insulin pump 14 may be configured to compute basal and bolus amounts and deliver the basal and bolus amounts accordingly. For instance, insulin pump 14 may determine the amount of a basal dosage to deliver continuously, and then determine the amount of a bolus dosage to deliver to reduce glucose level in response to an increase in glucose level due to eating or some other event. The term eating is used to generically refer to the act of consuming food and includes drinking as well.

Accordingly, in some examples, monitoring device 20 may sample glucose level for determining rate of change in glucose level over time. Monitoring device 20 may output the glucose level to insulin pump 14 (e.g., through a wireless link connection like Bluetooth or BLE). Insulin pump 14 may compare the glucose level to a target glucose level (e.g., as set by patient 12 or a clinician) and adjust the insulin dosage based on the comparison.

As described above, patient 12 or a clinician may set one or more target glucose levels on insulin pump 14. There may be various ways in which patient 12 or the clinician may set a target glucose level on insulin pump 14. As one example, patient 12 or the clinician may utilize patient device 24 to communicate with insulin pump 14. Examples of patient device 24 include mobile devices, such as smartphones, tablet computers, laptop computers, and the like. In some examples, patient device 24 may be a special programmer or controller (e.g., a dedicated remote control device) for insulin pump 14. Although FIG. 1 illustrates one patient device 24, in some examples, there may be a plurality of patient devices. For instance, system 10A may include a mobile device and a dedicated wireless controller, each of which is an example of patient device 24. For ease of description only, the example techniques are described with respect to patient device 24 with the understanding that patient device 24 may be one or more patient devices.

Patient device 24 may also be configured to interface with monitoring device 20. As one example, patient device 24 may receive information from monitoring device 20 through insulin pump 14, where insulin pump 14 relays the information between patient device 24 and monitoring device 20. As another example, patient device 24 may receive information (e.g., glucose level or rate of change of glucose level) directly from monitoring device 20 (e.g., through a wireless link).

In one or more examples, patient device 24 may comprise a user interface with which patient 12 or the clinician may control insulin pump 14. For example, patient device 24 may display a screen that allows patient 12 or the clinician to enter a target glucose level. Additionally or alternatively, patient device 24 may display a screen that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through a display of patient device 24 is merely provided as an example and should not be considered limiting. For example, insulin pump 14 may include pushbuttons that allow patient 12 or the clinician to set the various glucose levels of insulin pump 14. Also, in some examples, insulin pump 14 itself, or in addition to patient device 24, may be configured to output notifications to patient 12. For instance, if the current, sensed glucose level is too high or too low, insulin pump 14 may output an audible or haptic output. In some examples, if the battery is low, then insulin pump 14 may output a low battery indication on a display of insulin pump 14.

As mentioned above, insulin pump 14 may deliver insulin to patient 12 based on the current glucose level (e.g., as measured by monitoring device 20). However, it should be appreciated that insulin delivery is not limited to implementations based on current glucose levels. For example, insulin pump 14 may deliver insulin to patient 12 based on a predicted glucose level (e.g., a future glucose level that is determined based on a trend in glucose level).

The glucose level of patient 12 may be affected by patient 12 engaging in an activity like eating or exercising. There may be therapeutic benefits to delivering/not delivering insulin based on determining that patient 12 is engaging in the activity. For example, the change in the glucose level of patient 12 may be based on food intake and, particularly, the amount of carbohydrates in a meal and balance of carbohydrates in a meal. In general, the more carbohydrates there are in a meal, the higher the glucose level of patient 12 can go. However, even in a meal with relatively high amounts of carbohydrates, if there are sufficiently high amounts of protein and/or fiber, the rate at which the glucose level will increase and/or the highest the glucose level will reach may be less than the rate at which the glucose level will increase and/or the highest the glucose level will reach in meals with lower amounts of protein and/or fiber.

This disclosure describes example techniques for glucose level management based on predicting amounts of glucose to be absorbed into a bloodstream of patient 12 over a duration of time due to consumption of a meal. Predicting amounts of glucose to be absorbed into a bloodstream over a duration of time may also be referred to as predicting an "impact on glucose of carbohydrates." The predicted amounts of glucose to be absorbed into the bloodstream over a duration of time may be represented as a glucose profile (e.g., a time series of glucose levels). For instance, over time the amounts of glucose absorbed by the bloodstream may increase to a maximum and then decrease. Graphically, the amounts of glucose absorbed by the bloodstream over a duration of time can be represented as a line that trends upwards to a maximum and then decreases back down. This line of the amounts of glucose absorbed by the bloodstream over a duration of time may be referred to as a glucose profile indicative of how much (and how quickly) glucose is absorbed into the bloodstream at various points in time.

By predicting the amounts of glucose to be absorbed into the bloodstream over time, the example techniques may be used to determine one or more amounts of insulin to deliver to counteract the predicted amounts of glucose. For example, the example techniques described in this disclosure may be utilized to determine one or more amounts of insulin that even out the impact of the carbohydrates on the glucose level of patient 12. The one or more amounts of insulin may be delivered as a single dosage of insulin or as a plurality of dosages of insulin. In this manner, the example techniques may be used to keep the glucose level of patient 12 within a target range. In some cases, the example techniques may be used to keep the glucose level of patient 12 within a target range with minimal to no input from patient 12.

For example, one way in which to control diabetes is by having patient 12 enter, into a computing device (e.g., patient device 24 or insulin pump 14), information indicating an amount of carbohydrates patient 12 will consume/is consuming/did consume before/during/after a meal. Based on the entry of the amount of carbohydrates, one or more processors 28 may determine the impact on glucose of the carbohydrates and, thus, how much insulin to deliver to patient 12 to counteract the impact. However, patient 12 may fail to indicate or may fail to correctly indicate the amount of carbohydrates patient 12 will consume/is consuming/did consume. This may result in patient 12 failing to receive a bolus dosage or receiving an incorrect bolus dosage.

To avoid the aforementioned drawbacks, the techniques disclosed herein enable predicting the impact on glucose of carbohydrates without relying on patient 12 to provide an amount of carbohydrates included in a meal. As described in more detail below, this may be achieved based on contextual information (e.g., time of day, day of week, and/or geolocation) for the meal. Conceptually, the contextual information may be used to identify one or more previous meals that are similar to the meal. Thus, the impact on glucose of carbohydrates for the one or more previous meals can be used to estimate the impact on glucose of carbohydrates for the meal. For example, one or more processors 28 may predict the impact on glucose of carbohydrates for a Tuesday lunch at the company cafeteria will be similar or identical to the impact on glucose of carbohydrates for previous Tuesday lunches at the company cafeteria.

The predicted impact on glucose may be used to determine one or more amounts of insulin to counteract the predicted impact on glucose. For example, one or more processors 28 may determine one or more amounts of insulin that even out amounts of glucose predicted to be absorbed into the bloodstream of patient 12. The one or more amounts of insulin to counteract the predicted amounts of glucose may refer to one or more amounts of insulin for substantially maintaining glucose equilibrium (e.g., maintaining glucose levels within a predetermined range).

Counteracting or evening out the impact of carbohydrates may refer to approximately negating the increase in glucose level caused by consumption of carbohydrates to keep the glucose level in the predetermined range. For example, one or more processors 28 may determine an amount of insulin sufficient to maintain glucose in a desired range when the bloodstream absorbs the predicted amounts of glucose over time. In some examples, the amount of insulin may be a single dose of insulin (e.g., insulin pump 14 delivers that single dose of insulin all at once). In some examples, the amounts of insulin may be different doses of insulin to be delivered at different times (e.g., insulin pump 14 delivers small dosages of insulin over a period of time).

Although the above is described with respect to one or more processors 28 of FIG. 1, the example techniques are not so limited. The one or more processors configured to perform the example techniques described in the disclosure may include one or more processors 28 of cloud 26, one or more processors of patient device 24, one or more processors within insulin pump device 14, one or more processors of wearable device 22, and/or other processors. For ease of description, the example techniques are described with respect to one or more processors 28 of cloud 26.

As illustrated in FIG. 1, system 10A includes cloud 26 that includes one or more processors 28. For example, cloud 26 may include a plurality of network devices (e.g., servers), and each network device may include one or more processors. One or more processors 28 may be distributed across the plurality of network devices or may be located within a single one of the network devices. Cloud 26 represents a computing infrastructure that supports one or more processors 28 which may execute applications or operations requested by one or more users. For example, one or more processors 28 may remotely store, manage, and/or process data that would otherwise be locally stored, managed, and/or processed by patient device 24 or wearable device 22. One or more processors 28 may share data or resources for performing computations and may be part of computing servers, web servers, database servers, and the like. One or more processors 28 may be in network devices (e.g., servers) within a data center or may be distributed across multiple data centers. In some cases, the data centers may be in different geographical locations.

One or more processors 28, as well as other processing circuitry described herein, can include one or more of any of the following: microprocessors, digital signal processors (DSPs), application specific integrated circuits (ASICs), field programmable gate arrays (FPGAs), or any other equivalent integrated or discrete logic circuitry, as well as any combinations of such components. The functions attributed to one or more processors 28, as well as other processing circuitry described herein may be embodied as hardware, firmware, software, or any combination thereof.

One or more processors 28 may be implemented as fixed-function circuits, programmable circuits, or a combination thereof. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more processors 28 may include distinct circuit blocks (fixed-function or programmable), and in some examples, one or more processors 28 may include integrated circuits. One or more processors 28 may include arithmetic logic units (ALUs), elementary function units (EFUs), digital circuits, analog circuits, and/or programmable cores formed from programmable circuits. In examples where the operations of one or more processors 28 are performed using software executed by the programmable circuits, memory (e.g., on servers in cloud 26) accessible by one or more processors 28 may store the object code of the software that one or more processors 28 receive and execute.

As described above, one or more processors 28 may be configured to predict, based on contextual information, the impact on glucose of carbohydrates included in a meal. For example, patient 12 may activate a physical or software-implemented button via insulin pump 14 or patient device 24 to provide an indication of a meal occurrence, and responsive to receiving the indication, one or more processors 28 may predict the impact based on contextual information for the meal occurrence. In some examples, a meal occurrence may be determined automatically to further reduce user burden. For example, one or more processors 28 may determine that a meal occurrence without patient 12 providing an indication of the meal occurrence. This may be achieved based on a variety of data, examples of which include contextual information (e.g., time of day, day of week, and/or geolocation), an amount of time since patient 12 last ate, a sharp increase in glucose level of patient 12, and/or gesture information (e.g., of arm/hand movement) indicative of patient 12 eating.

As illustrated in FIG. 1, patient 12 may wear wearable device 22. Examples of wearable device 22 include a smartwatch or a fitness tracker, either of which may, in some examples, be configured to be worn on a patient's wrist or arm. In one or more examples, wearable device 22 includes an inertial measurement unit, such as a six-axis inertial measurement unit. The inertial measurement unit may include an accelerometer (e.g., a 3-axis accelerometer) and a gyroscope (e.g., a 3-axis gyroscope). Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. For example, patient 12 may wear wearable device 22 on a finger, forearm, or bicep. In general, patient 12 may wear wearable device 22 anywhere that can be used to determine gestures indicative of eating.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency with which patient 12 moves his or her arm or a pattern with which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect any activity undertaken by patient 12. For instance, the movement characteristics detected by wearable device 22 may indicate whether patient 12 is exercising, driving, sleeping, etc. In some examples, wearable device 22 may detect a posture of patient 12 that corresponds with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to one or more other devices (e.g., patient device 24 and/or one or more server computers in cloud 26), and the one or more other devices may be configured to determine the activity patient 12 is undertaking.

In some examples, one or more processors 28 may be configured to determine patterns from gesture movements (e.g., one or more movement characteristics determined by wearable device 22) and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). For example, patient device 24 may output, to cloud 26, information indicative of the movement characteristics of patient 12 with contextual information like location and/or time of day, and one or more processors 28 may determine the activity patient 12 is undertaking. Cloud 26 and patient device 24 may communicate via one or more networks (e.g., a wired network, a wireless network, and/or a carrier network).

One example way in which one or more processors 28 may be configured to determine that patient 12 is undertaking an activity and determine therapy to deliver is described in U.S. Patent Publication No. 2020/0135320 A1, the entirety of which is incorporated by reference herein. The above describes arm movement as a factor in determining whether patient 12 is engaging in an activity. However, there may be various other factors that can be used separately or in combination with arm movement to determine whether patient 12 is engaging in an activity. Time of day and location are two examples of contextual information that can be used to determine whether patient 12 is engaging in the activity. For instance, patient 12 may engage in the activity at regular time intervals and/or at certain locations. Such other factors may be communicated to one or more processors 28 in any of a variety of ways. For example, patient device 24 may output information about the time of day and the location of patient 12. In some examples, patient device 24 may be equipped with a positioning device, such as a global positioning system (GPS) unit, and patient device 24 may output location information determined by the GPS unit. In some examples, location information may be determined based on known locations of wireless access points and/or cell towers.

There may be various other ways in which one or more processors 28 may determine the activity patient 12 is undertaking. This disclosure provides some example techniques for determining the activity patient 12 is undertaking, but the example techniques should not be considered limiting.

Turning back to the discussion of techniques for using contextual information to predict the impact on glucose of carbohydrates in a meal, in accordance with one or more examples described in this disclosure, one or more processors 28 may be configured to predict amounts of glucose to be absorbed into a bloodstream of patient 12 over a duration of time due to consumption of the meal. This may be achieved based on a "learning" phase during which one or more processors 28 may determine a correlation between contextual information and the impact on glucose of carbohydrates in a number of meals.

As described in more detail below, one or more processors 28 may have access to a physiological model of patient 12. The physiological model may comprise one or more differential equations having one or more patient-specific parameters (e.g., an insulin sensitivity factor and/or an insulin-to-carbohydrate ratio). Among other things, the physiological model may correlate any number of the following information with amounts of glucose absorbed into the bloodstream over a duration of time due to the consumption of a meal:

- a time series of interstitial glucose level measurements (e.g., obtained from monitoring device 20); and
- an amount of a meal bolus (e.g., a bolus dosage of insulin delivered around the time of a meal occurrence).

Thus, the physiological model may be used to calculate (e.g., back-calculate) the impact on glucose of carbohydrates included in one or more meals (e.g., one or more previous meals). Advantageously, this technique can be performed regardless of whether carbohydrate information is available for the one or more meals. Accordingly, training data may comprise contextual information; interstitial glucose level measurements; and/or meal bolus information. Based on the training data, one or more processors 28 may be configured to determine a correlation between the contextual information and amounts of glucose absorbed into the bloodstream of patient 12 over a duration of time due to meal consumption (e.g., an amount of glucose absorbed into the bloodstream after 10 seconds, an amount of glucose absorbed into the bloodstream after 20 seconds, and so forth).

For example, during a learning phase, when patient 12 has a meal, one or more processors 28 may obtain and/or record (e.g., maintain) a set of interstitial glucose levels measured over a duration of time (e.g., from monitoring device 20), an amount of insulin delivered to patient 12 (e.g., from insulin pump 14) to counteract a glucose level increase caused by consumption of the meal, a time of the meal (e.g., from patient device 24), a location of the meal (e.g., from patient device 24), and/or any other data related to the meal (e.g., biosensor data indicative of temperature, pulse/heart rate, breathing rate, etc.). Based on the set of interstitial glucose levels and the amount of insulin delivered to patient 12, one or more processors 28 may calculate amounts of glucose absorbed into the bloodstream over the duration of time due to the consumption of the meal. The calculated amounts of glucose absorbed into the bloodstream over a duration of time due to the consumption of the meal and the associated contextual data (e.g., time of meal, location, biosensor data, etc.) may be inputs into a machine learning model (e.g., a k-means clustering model) to train the machine learning model and generate a trained model (e.g., a correlation between calculated amounts of glucose absorbed into the bloodstream and contextual information for one or more meals). Thus, when contextual data for another meal is provided as input to the trained machine learning model, the output may be a prediction of the amounts of glucose to be absorbed into the bloodstream of the patient over a duration of time due to the consumption of that other meal.

In some examples, the correlation determined between contextual information and amounts of glucose absorbed into the bloodstream may be refined based on "ground truth" data. For example, the accuracy of predicted amounts of glucose to be absorbed into the bloodstream may be determined based on comparison with back-calculated amounts of glucose absorbed into the bloodstream. To illustrate with continued reference to the example of the preceding paragraph, actual amounts of glucose absorbed into the bloodstream may be back-calculated based on a set of interstitial glucose level measurements and an amount of insulin delivered in relation to that other meal, and the actual amounts may be compared against the predicted amounts to determine the accuracy of the prediction.

In some examples, the correlation may be modeled using weighted parameters, and refining the correlation may involve updating weights such that for a given input, the output from machine learning model is approximately equal to the ground-truth. For example, one or more processors 28 may determine weights of the machine learning model such that if the input of the machine learning model is contextual information, the output (e.g., predicted amounts of glucose to be absorbed into the bloodstream) equals the ground-truth (e.g., back-calculated amounts of glucose absorbed into the bloodstream of patient 12).

The above describes the example of using a machine learning model to predict the amounts of glucose to be absorbed into the bloodstream of patient 12 over a duration of time due to the consumption of a meal. However, there may be other example ways in which one or more processors 28 may predict the amounts of glucose to be absorbed into the bloodstream of patient 12 over a duration of time due to the consumption of a meal. For example, one or more processors 28 may utilize statistical averaging techniques and/or pattern matching techniques.

In statistical averaging techniques, based on contextual information, one or more processors 28 may determine which of a plurality of possible amounts of glucose has the highest statistical probability of being the amounts of glucose to be absorbed into the bloodstream for a particular meal. For example, if the contextual information indicates that there is a high statistical probability that patient 12 is going to be eating some type of food that generates a particular glucose profile (e.g., is associated with certain amounts of glucose that is absorbed into the bloodstream of patient 12 over a duration of time due to the consumption of meal), one or more processors 28 may determine that glucose profile having the highest statistical probability as indicative of the amounts of glucose to be absorbed into the bloodstream of patient 12 over the duration of time due to the consumption of the meal.

In pattern matching, one or more processors 28 may determine whether there is any pattern indicative of a correlation between contextual information and amounts of glucose to be absorbed into the bloodstream of patient 12 over a duration of time due to the consumption of a meal. For example, patient 12 may have a predisposition to eat a burger for lunch on Mondays, a taco for lunch on Tuesdays, a pizza for lunch on Wednesdays, etc. Based on there being a matching pattern, one or more processors 28 may predict the amounts of glucose to be absorbed into the bloodstream of patient 12 over a duration of time.

Machine learning, statistical averaging, and pattern matching are example techniques for predicting amounts of glucose to be absorbed into a bloodstream of patient 12 over a duration of time due to consumption of the meal based on contextual information. However, the example techniques should not be considered limiting, and other techniques may be utilized as well. Machine learning, statistical averaging, and pattern matching are all examples of artificial intelligence techniques, and the examples described in the disclosure may utilize any number of the various examples of artificial intelligence techniques.

In one or more examples, one or more processors 28 may determine one or more amounts of insulin to counteract the (e.g., effect of) predicted amounts of glucose to be absorbed into the bloodstream over the duration of time. For example, one or more processors 28 may calculate one or more amounts of insulin that would approximately negate an increase in glucose level due to meal consumption such that the sensed glucose level (e.g., from monitoring device 20) remains within a predetermined target range. That is, the one or more amounts of insulin may substantially maintain glucose equilibrium (e.g., maintaining glucose levels within a predetermined range) based on counteracting the change in glucose levels due to the predicted amounts of glucose to be absorbed into the bloodstream over the duration of time.

An example way in which to determine the one or more amounts of insulin is with a patient-specific physiological simulator referred to herein as a "digital twin." One or more processors 28 may be configured to utilize a "digital twin" of patient 12 to determine, in a manner that accounts for various idiosyncrasies of patient 12, the one or more amounts of insulin patient 12 is to receive. A digital twin may be a digital replica of a patient that is based on a mathematical model having one or more patient-specific parameters (e.g., an insulin-to-carbohydrate ratio and/or an insulin sensitivity factor). The digital twin may be implemented via software executing on one or more processors 28. The digital twin may obtain information about the predicted amounts of glucose to be absorbed into the bloodstream over the duration of time and use this information to determine a recommendation of how much insulin (e.g., an amount of a bolus dosage) to deliver to patient 12 to control an increase in glucose level.

For example, an insulin dosage recommendation may be determined based on using the digital twin to simulate the effectiveness of one or more candidate dosages in counteracting the predicted amounts of glucose. Each candidate dosage may be provided as input to the digital twin, which predicts a time series of glucose levels based on the candidate dosage and the predicted amounts of glucose to be absorbed into the bloodstream over the duration of time. The time series of glucose levels may be evaluated to determine how much time (e.g., of the duration of time) is spent within a target range. The candidate dosage that is selected for recommendation may correspond to a maximum amount of time (e.g., relative to predicted glucose levels resulting from one or more other candidate dosages) within a target range for the patient's glucose levels. As used herein, the term "optimal" is used to describe a dosage that exhibits such a characteristic.

Additionally or alternatively, artificial intelligence techniques may be used to determine an optimal dosage. Such techniques may leverage the digital twin or some other physiological model.

In some examples, the optimal dosage may be determined using artificial intelligence techniques similar to those discussed above for determining the predicted amounts of glucose to be absorbed into the bloodstream. For example, as mentioned above, the digital twin may be used to determine the correct (e.g., optimal) dosage for a meal, and this is equally applicable for meals that patient 12 ate in the past. Thus, one or more processors 28 may utilize the digital twin to generate training data that includes optimal dosages that have been back-calculated for previous meals. Based on the training data, one or more processors 28 may determine a correlation between contextual information (and/or the predicted amounts of glucose to be absorbed into the bloodstream) and optimal dosages, thereby enabling optimal dosages to be quickly recommended for similar meals in the future.

In some examples, the optimal dosage may be determined using genetic programming. For example, one or more processors 28 may form a neural network configured to generate a mathematical model for determining the optimal dosage based on the predicted amounts of glucose to be absorbed into the bloodstream.

One or more processors 28 may be configured to affect insulin therapy based on outputting information indicative of the determined one or more amounts of insulin. For example, one or more processors 28 may communicate towards an insulin delivery device, like insulin pump 14, the information indicative of the determined one or more amounts of insulin and/or communicate towards the insulin delivery device information indicative of times when the insulin delivery device is to deliver the determined one or more amounts of insulin. Insulin pump 14 may then automatically deliver (e.g., with minimal to no patient interaction) the determined one or more amounts of insulin to patient 12 based on the information indicative of the determined amounts of insulin and/or the information indicative of the times when the insulin delivery device (e.g., insulin pump 14) is to deliver the determined amounts of insulin.

The term "communicate towards" as used in the disclosure may refer to ways in which a device may receive information from another device. For instance, although possible, in some examples, one or more processors 28 may not be configured to directly communicate with insulin pump 14. In such examples, one or more processors 28 may communicate towards insulin pump 14 by outputting information to patient device 24, which relays the information to insulin pump 14.

The above example techniques are described as being performed by one or more processors 28 that are included in one or more network devices of cloud 26. However, the example techniques are not so limited. The one or more processors configured to perform the example techniques described in this disclosure may be one or more processors 28, one or more processors of patient device 24, one or more processors of wearable device 22, and/or one or more processors of insulin pump 14. System 10A may also include one or more processor-readable storage media (e.g., memory of network devices of cloud 26, memory of patient device 24, memory of wearable device 22, and/or memory of insulin pump 14). The one or more processor-readable storage media may store instructions which, when executed by the one or more processors, cause performance of the example techniques described in this disclosure.

Figure 2:
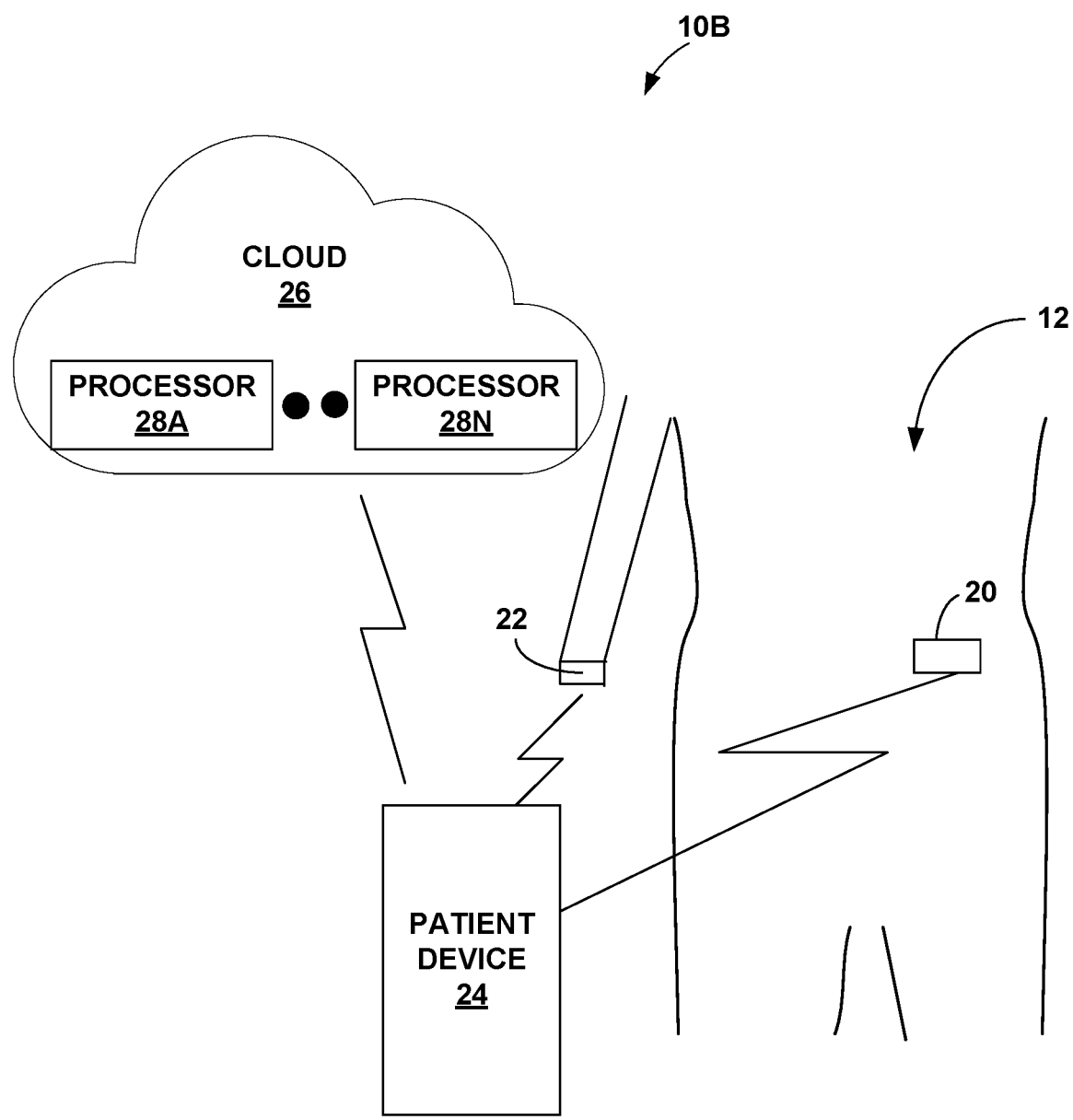
FIG. 2 is a block diagram illustrating an example glucose level management system comprising a manual injection device, in accordance with one or more examples described in this disclosure.

FIG. 2 is a block diagram illustrating an example glucose level management system comprising a manual injection device (not shown), in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or a syringe) to deliver insulin. For example, rather than insulin pump 14 automatically delivering insulin, patient 12 (or a caretaker of patient 12) may fill a syringe with insulin, set the dosage amount in an insulin pen, and/or perform an injection.

The example of FIG. 2 may operate in substantially the same manner as the example techniques described above in FIG. 1. However, in system 10B, since there is no insulin pump 14, patient 12 may receive a notification on patient device 24 that indicates the one or more amounts of insulin to counteract effects of the predicted amounts of glucose to be absorbed into the bloodstream over the duration of time and/or information that indicates when patient 12 is to receive the amounts of insulin. That is, affecting (e.g., guiding, causing, instructing, determining) insulin therapy based on outputting information indicative of the determined amounts of insulin may include communicating to patient device 24 information indicative of the one or more amounts of insulin and/or information of times when patient 12 is to receive the insulin. Patient 12 or a caretaker of patient 12 may then provide therapy accordingly.

Figure 3:
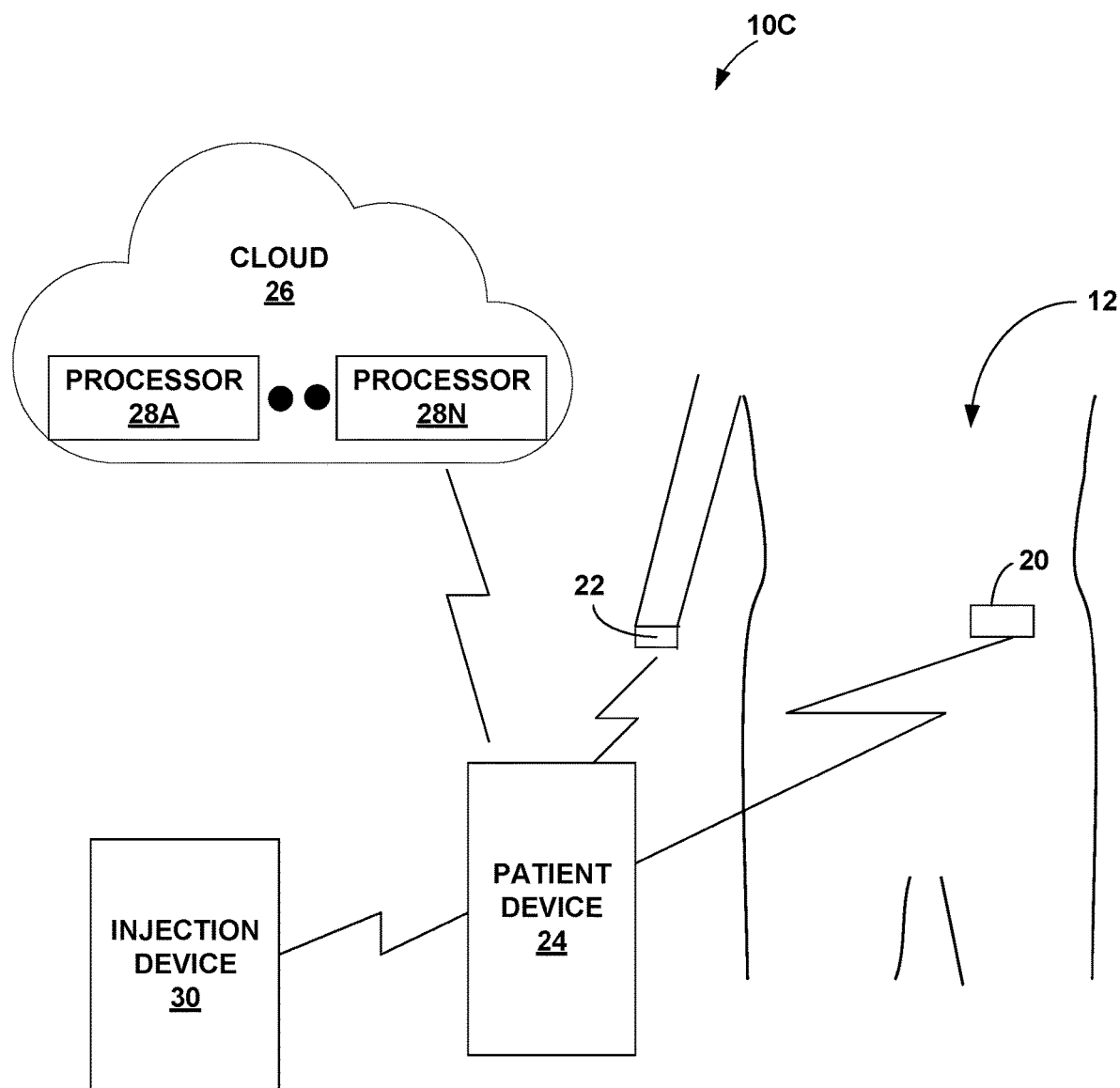
FIG. 3 is a block diagram illustrating an example glucose level management system comprising a networked injection device, in accordance with one or more examples described in this disclosure.

FIG. 3 is a block diagram illustrating an example glucose level management system comprising a networked injection device, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or a caretaker of patient 12) may utilize injection device 30 to perform an injection.

Injection device 30 may be different than a syringe because injection device 30 may be a device that can communicate with patient device 24 and/or other devices in system 10C. Also, injection device 30 may include a reservoir and, based on information indicative of how much therapy dosage to deliver, may be able to dose out that much insulin for delivery. For example, injection device 30 may automatically set the amount of insulin based on the information received from patient device 24. In some examples, injection device 30 may be similar to insulin pump 14 but not worn by patient 12. One example of injection device 30 is an insulin pen, sometimes also called a smart insulin pen. Another example of injection device 30 may be an insulin pen with a smart cap, where the smart cap can be used to set particular doses of insulin.

In the example of FIG. 3, for system 10C, affecting insulin therapy based on outputting information indicative of the determined one or more amounts of insulin may include communicating towards an insulin delivery device the information indicative of the determined one or more amounts of insulin. In system 10C, the insulin delivery device is injection device 30 configured to automatically set an insulin level based on the information indicative of the determined one or more amounts of insulin.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be a powered (e.g., battery-powered) device, and the syringe may be a device that requires no power.

Figure 4:
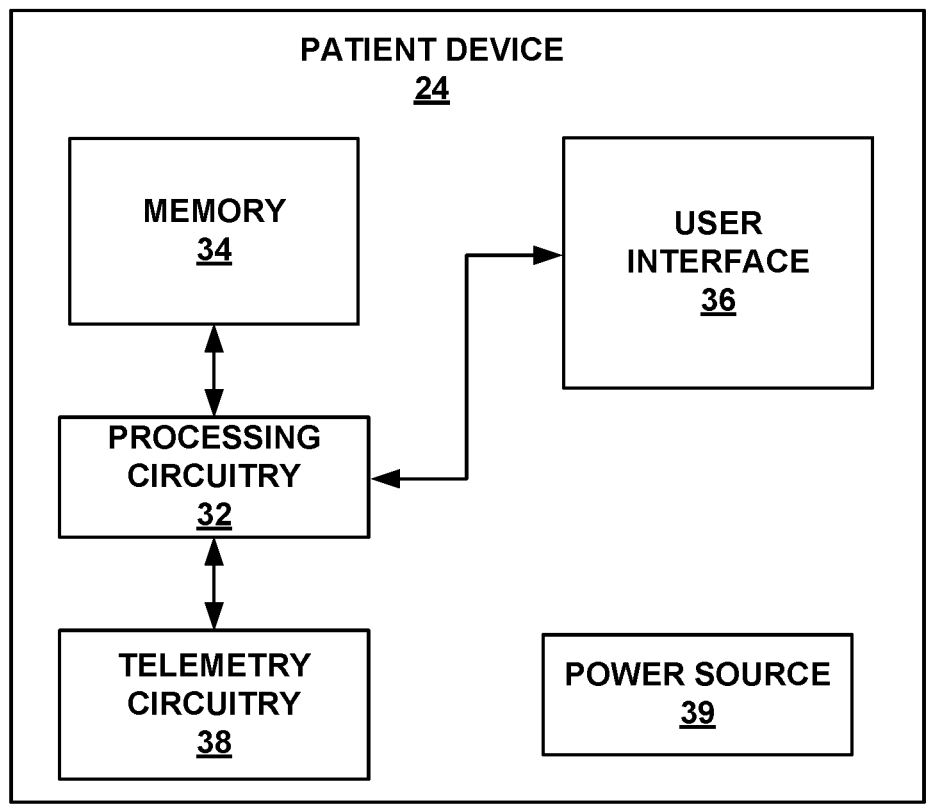
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, patient device 24 may be a notebook computer or a workstation, for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be a specialized controller for communicating with insulin pump 14.

As illustrated in FIG. 4, patient device 24 may include a processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure. For example, memory 34 is an example of processor-readable storage media storing instructions which, when executed by processing circuitry 32, cause performance of one or more examples described in this disclosure.

In some examples, memory 34 of patient device 24 may store a plurality of parameters, such as amounts of insulin to deliver, target glucose level, time of delivery, etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification to take insulin, amount of insulin, and time to take the insulin, via user interface 36.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a microphone for voice commands, and/or a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text via the keypad, or selecting an icon from a touchscreen. The patient input may be information indicative of a meal event, whether patient 12 took the insulin (e.g., through the syringe or injection device 30), and other such information.

Telemetry circuitry 38 includes any suitable hardware, firmware, software, or any combination thereof for communicating with another device, such as cloud 26, insulin pump 14 or injection device 30, as applicable, wearable device 22, and monitoring device 20. Telemetry circuitry 38 may receive communication with the aid of an antenna, which may be internal and/or external to patient device 24. Telemetry circuitry 38 may be configured to communicate with another computing device via wireless communication techniques or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may last for several months or years, while a rechargeable battery may be periodically charged from an external device, e.g., on a daily or weekly basis. Recharging of a rechargeable battery may be accomplished by using an alternating current (AC) outlet or through proximal inductive interaction between an external charger and an inductive charging coil within patient device 24.

As described above, one or more processors may be configured to obtain contextual information for a meal, where examples of the contextual information include one or more of a group comprising a time of day, a day of week, and a patient location. In some examples, processing circuitry 32 may be configured to output the time of day, day of week, and/or patient location (e.g., based on positioning information (e.g., GPS) or network connectivity information) to one or more processors 28.

Figure 5:
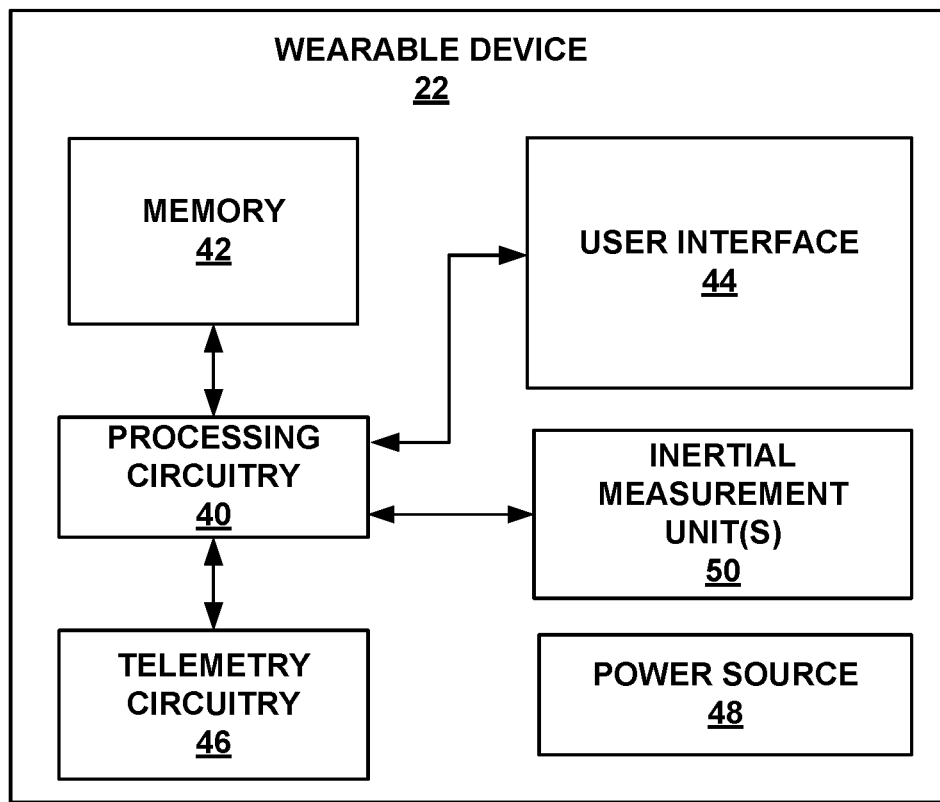
FIG. 5 is a block diagram illustrating an example of a wearable device, in accordance with one or more examples described in this disclosure.

FIG. 5 is a block diagram illustrating an example of a wearable device, in accordance with one or more examples described in this disclosure. As illustrated, wearable device 22 includes processing circuitry 40, memory 42, user interface 44, telemetry circuitry 46, power source 48, and inertial measurement unit(s) 50. Processing circuitry 40, memory 42, user interface 44, telemetry circuitry 46, and power source 48 may be similar to processing circuitry 32, memory 34, user interface 36, telemetry circuitry 38, and power source 39 of FIG. 4, respectively.

Inertial measurement unit(s) 50 may include gyroscopes and/or various components to determine a pitch-roll-yaw and x-y-z coordinate of wearable device 22. In some examples, inertial measurement unit(s) 50 may include a six-axis inertial measurement unit. For example, inertial measurement unit(s) 50 may include a 3-axis accelerometer and a 3-axis gyroscope. The accelerometer may measure linear acceleration, while the gyroscope may measure rotational motion. Processing circuitry 40 may be configured to determine one or more movement characteristics based on values from inertial measurement unit(s) 50. For example, processing circuitry 40 may determine, based on values from inertial measurement unit(s) 50, if patient 12 is moving his or her arm upwards, downwards, leftwards, rightwards, forwards, backwards, or some combination. Processing circuitry 40 may also be configured to determine values related to frequency, amplitude, trajectory, position, velocity, acceleration, and/or pattern of movement. For example, processing circuitry 40 may determine, based on values from inertial measurement unit(s) 50, orientation of the arm of patient 12, such as whether the back of the hand or the front of the hand is facing patient 12, or if a side of the hand is facing patient 12 such that the thumb is facing patient 12 and the side of the index finger is visible.

Inertial measurement unit(s) 50 may output such information (e.g., pitch-roll-yaw and x-y-z coordinates) of the arm of patient 12 to processing circuitry 40. Telemetry circuitry 46 may then output the information from processing circuitry 40 to patient device 24. Patient device 24 may forward the information to one or more processors 28 that can use the information to determine if patient 12 is eating (e.g., if a meal event is occurring). One or more processors 28 may then utilize the information to determine that patient 12 is consuming a meal based on the information, and responsive to determining that the patient is consuming a meal, predict amounts of glucose to be absorbed into a bloodstream of the patient over a duration of time due to consumption of the meal based on the contextual information.

Figure 6:
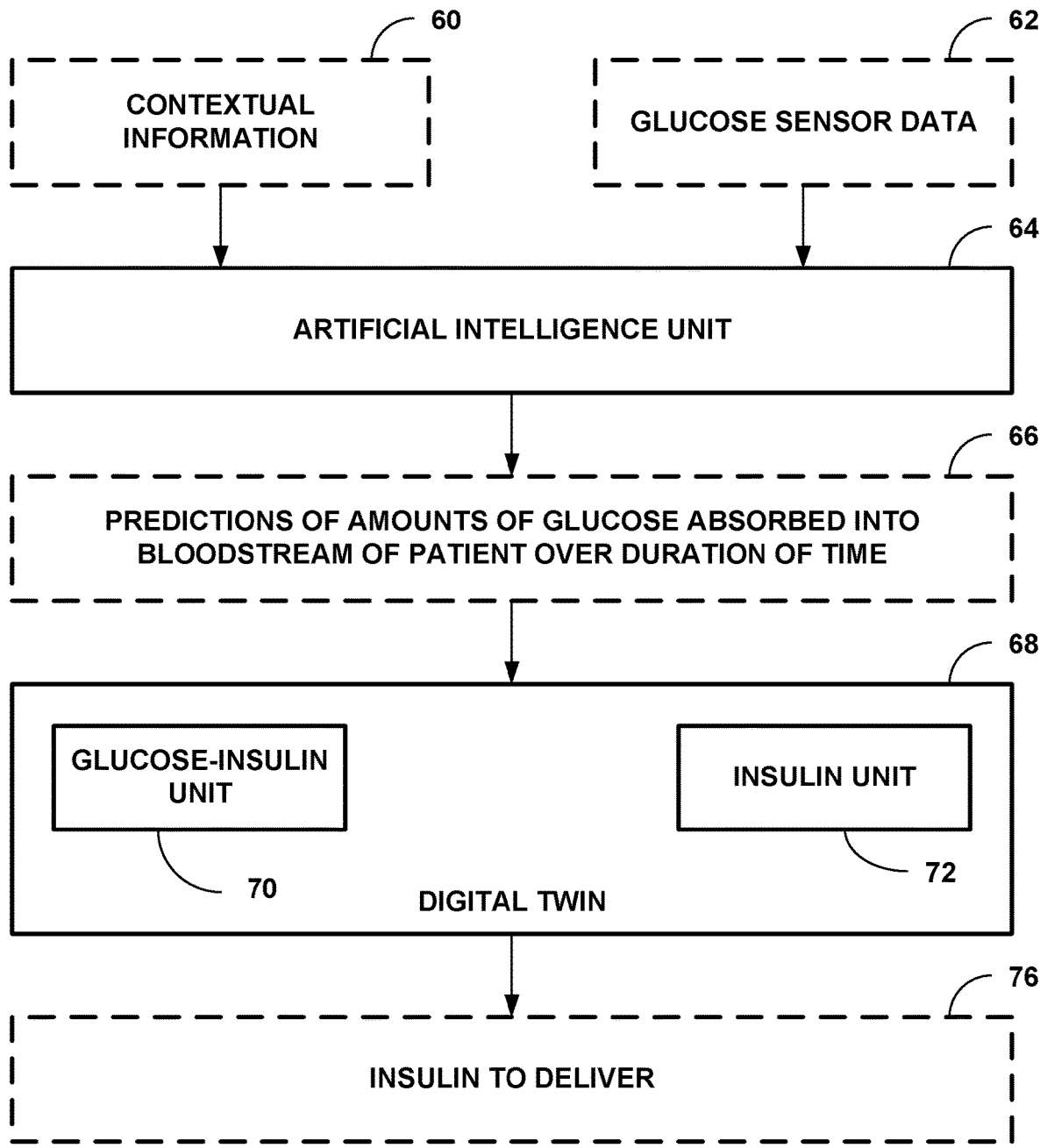
FIG. 6 is a conceptual diagram illustrating an example data flow for determining an amount of insulin to be delivered to a patient.

FIG. 6 is a conceptual diagram illustrating an example data flow for determining an amount of insulin to be delivered to a patient. In FIG. 6, the dashed lines represent data that is processed by one or more processors (e.g., one or more processors 28, processing circuitry 32, processing circuitry 40, and/or processing circuitry of insulin pump 14).

As illustrated, artificial intelligence unit 64 may receive contextual information 60 and glucose sensor data 62. Artificial intelligence unit 64 can be implemented using software, hardware, and/or firmware (e.g., one or more processors and one or more processor-readable storage media storing instructions configured to perform artificial intelligence techniques such as a statistical average technique, a pattern matching technique, and/or a machine learning technique). For example, during a learning phase, artificial intelligence unit 64 may use glucose sensor data 62 and insulin delivery data to determine a correlation between contextual information 60 and predictions 66 of amounts of glucose to be absorbed into the bloodstream of a patient over a duration of time due to meal consumption. Based on this correlation and contextual information 60, artificial intelligence unit 64 may generate predictions 66 for other meals.

The following describes one example way in which artificial intelligence unit 64 may determine the correlation. During the learning phase, when patient 12 indicates a meal event, the one or more processors may track any number of the following:

glucose sensor data 62 (e.g. glucose levels sensed by monitoring device 20 every 5 minutes for 240 minutes for 48 measurement);
 an amount of a meal bolus delivered to patient 12; and
 contextual information 60.

The learning phase may be performed based on multiple meal events (e.g., a few meals to hundreds of meals, and there may be continuous learning even after the learning phase). Artificial intelligence unit 64 may maintain the tracked information for each of the multiple meal events.

A physiological model of patient 12 may be used to generate training data based on the tracked information. For example, for each meal, glucose sensor data 62 and the amount of the meal bolus may be used to back-calculate amounts of glucose absorbed into the bloodstream of patient 12 over a duration of time. Artificial intelligence unit 64 may determine a correlation between the back-calculated amounts of glucose and contextual information 60 (e.g., time of day, location, etc.) using statistical averaging, pattern matching, and/or machine learning.

As illustrated in FIG. 6, digital twin 68 may receive predictions 66. Digital twin 68 may comprise a set of differential equations that receives as input predictions 66 and outputs one or more amounts of insulin 76 to deliver to counteract the effects of the predicted amounts of glucose to be absorbed into the bloodstream. Digital twin 68 may be implemented as software executing on one or more processors.

Digital twin 68 may include glucose-insulin unit 70 and insulin unit 72. In some examples, artificial intelligence unit 64 may include digital twin 68.

Insulin unit 72 may determine, for a given "input insulin amount" (e.g., amount of insulin delivered subcutaneously), how much insulin will enter the bloodstream of patient 12 over time. Insulin unit 72 may be particularized for patient 12 so that insulin unit 72 outputs patient-specific information indicative of how much insulin will enter the bloodstream of patient 12.

How much insulin will be absorbed into the bloodstream over time may be represented as an "insulin profile." For example, the insulin profile may indicate that after one minute, there will be X amount of insulin absorbed in the bloodstream, after two minutes, there will be Y amount of insulin absorbed in the bloodstream, and so forth. Different input insulin amounts may exhibit different insulin profiles.

In one or more examples, insulin unit 72 may utilize a selected (e.g., pre-selected or predetermined based on one or more factors) set of input insulin amounts to be delivered. For each insulin amount in the set, insulin unit 72 may determine how much insulin will be absorbed into the bloodstream over time.

Glucose-insulin unit 70 may model the interaction between glucose levels, insulin in the bloodstream, and amounts of glucose absorbed into the bloodstream over a duration of time. For example, glucose-insulin unit 70 may receive, from artificial intelligence unit 64, predictions 66 and receive, from insulin unit 72, insulin profile information. Based on the output from artificial intelligence unit 64 and insulin unit 72, glucose-insulin unit 70 may determine what the glucose levels for patient 12 will be over time. In some examples, glucose-insulin unit 70 may be personalized for patient 12 based on factoring the insulin sensitivity of patient 12 into its model(s).

As an example, the target range of the glucose level of patient 12 may be within 180 dl/mg and 90 dl/mg. Glucose-insulin unit 70 may indicate what the glucose level of patient 12 will be over time and thus whether the glucose level will be outside the target range and for how much of the time.

As mentioned above, glucose-insulin unit 70 may receive insulin profile information and receive predictions 66. For each insulin profile, glucose-insulin unit 70 may generate information indicative of time in target range (e.g., for how long the glucose level of patient 12 will be within a desired maximum and minimum). Glucose-insulin unit 70 may select the insulin profile that provides the longest time in target range, and glucose-insulin unit 70 may determine the amount or amounts of insulin associated with the selected insulin profile as the amount or amounts of insulin that are to be delivered to patient 12 to counteract effects of the predicted amounts of glucose to be absorbed into the bloodstream of patient 12 over the duration of time.

The output from digital twin 68 may be information indicative of one or more amounts of insulin 76 to deliver. For example, one or more processors 28 may affect insulin therapy based on outputting information indicative of the determined one or more amounts of insulin 76. The one or more processors may communicate toward (e.g., via patient device 24) an insulin delivery device (e.g., insulin pump 14 or injection device 30) the information indicative of the determined one or more amounts of insulin 76. Injection device 30 may be configured to automatically set an insulin level based on the information indicative of the determined one or more amounts of insulin 76. Insulin pump 14 may be configured to automatically deliver the determined one or more amounts of insulin 76 to patient 12 (e.g., over time) based on the information indicative of the determined one or more amounts of insulin 76 and/or information (e.g., received from the one or more processors) indicative of the times when insulin pump 14 is to deliver the determined one or more amounts of insulin 76.

Figure 7:
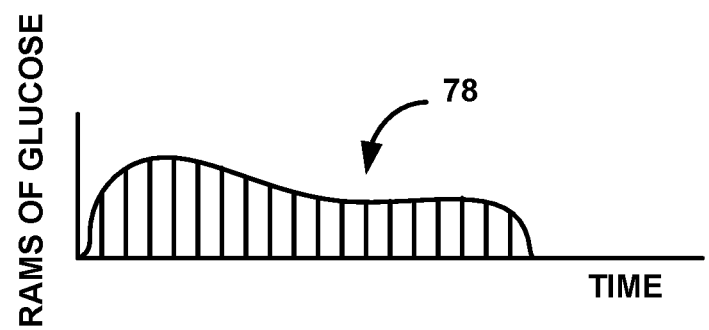
FIG. 7 is a conceptual diagram illustrating an example of information indicative of predicted amounts of glucose to be absorbed into the bloodstream of a patient over a duration of time.

FIG. 7 is a conceptual diagram illustrating an example of information indicative of predicted amounts of glucose to be absorbed into the bloodstream of a patient over a duration of time. In the example of FIG. 7, the x-axis is time and the y-axis is grams of glucose that are to be absorbed into the bloodstream of patient 12. For example, line 78 represents predictions of amounts of glucose to be absorbed into a bloodstream of patient 12 over a duration of time due to consumption of a meal based on contextual information.

Line 78 is an example of a glucose profile that artificial intelligence unit 64 may generate. As illustrated, line 78 of FIG. 7 is based on a line that connects a plurality of points. Each of the points represents an amount of glucose to be absorbed into the bloodstream at a particular instance in time within the duration of time. For example, predicting the amounts of glucose includes the one or more processors predicting a first amount of glucose to be absorbed into the bloodstream at a first time instance within the duration of time (e.g., the first point in line 78), and predicting a second amount of glucose to be absorbed into the bloodstream at a second time instance within the duration of time (e.g., the second point in line 78), and so on.

Figure 8:
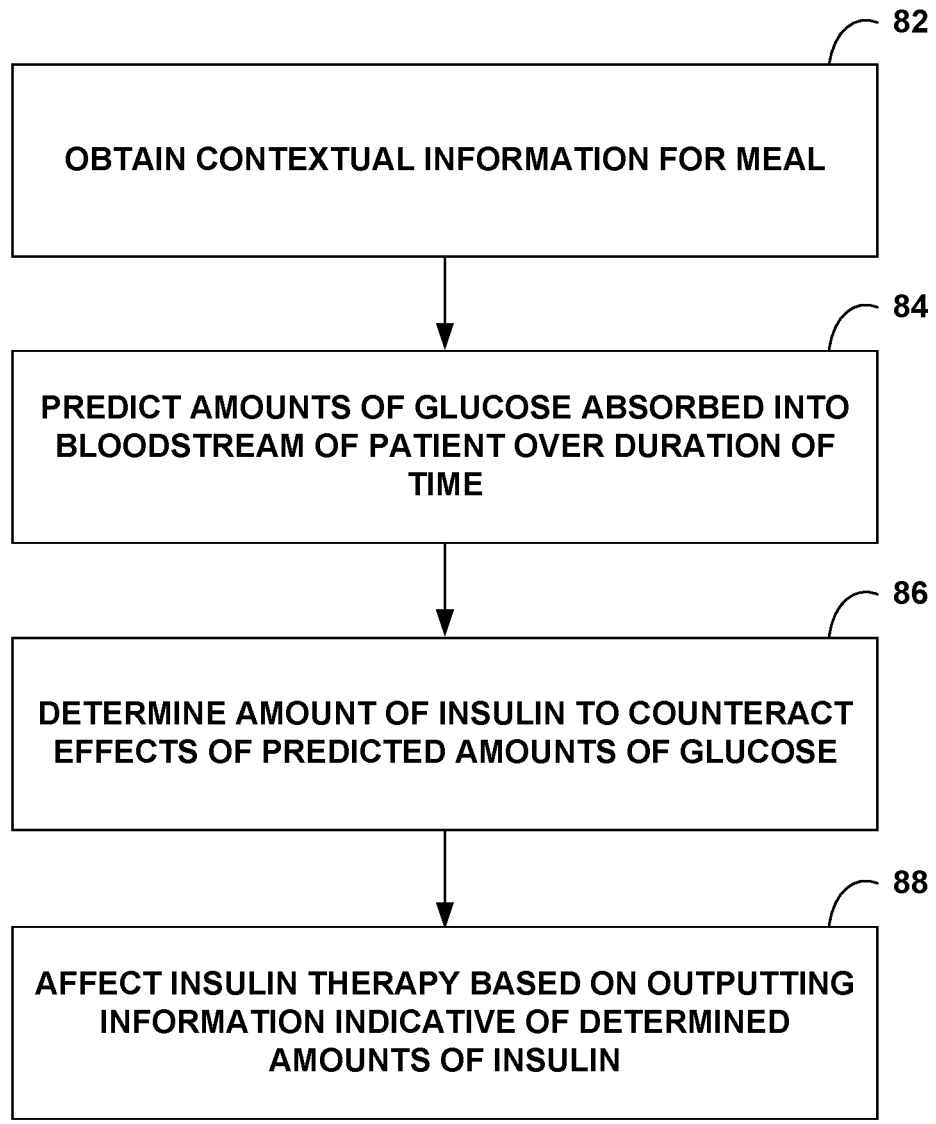
FIG. 8 is a flowchart illustrating an example process for glucose level management without carbohydrate counting.

FIG. 8 is a flowchart illustrating an example process for glucose level management without carbohydrate counting. The example techniques are described with respect to one or more processors such as one or more processors 28, processing circuitry 32, processing circuitry 40, and/or one or more processors of insulin pump 14.

The one or more processors may be configured to obtain contextual information for a meal (82). The contextual information may include one or more of a group comprising a time of day, a day of week, and a patient location. The contextual information may be obtained responsive to receiving (e.g., at patient device 24) user input indicating a meal event. Additionally or alternatively, the contextual information may be obtained responsive to receiving (e.g., at patient device 24) gesture information from wearable device 22 indicating that movement characteristics of patient 12 align with movement characteristics of patient 12 when patient 12 is eating. The one or more processors may determine that patient 12 is to consume a meal based on the gesture information.

In one or more examples, the one or more processors may predict amounts of glucose to be absorbed into a bloodstream of patient 12 over a duration of time due to consumption of the meal based on the contextual information for the meal (84). As illustrated in FIG. 7, with line 78, predicting the amounts of glucose may include predicting a first amount of glucose to be absorbed into the bloodstream at a first time instance within the duration of time (e.g., first point in line 78) and predicting a second amount of glucose to be absorbed into the bloodstream at a second time instance within the duration of time (e.g., second point in line 78), and so on.

In some examples, predicting the amounts of glucose to be absorbed into the bloodstream of the patient is performed without information from patient 12 of carbohydrates consumed from the meal (e.g., to minimize burden on patient 12). Because information of the carbohydrates consumed from the meal is not available from patient 12 in such examples, the one or more processors may predict the amounts of glucose to be absorbed by utilizing one or more of a group comprising a statistical averaging technique, a pattern matching technique, and a machine learning technique. For example, prior to predicting the amounts of glucose to be absorbed into the bloodstream, the one or more processors may determine a correlation between contextual information for one or more previous meals and amounts of glucose absorbed into the bloodstream of patient 12 over a duration of time due to consumption of the one or more previous meals. The correlation may be determined without information from patient 12 relating to carbohydrates consumed from the one or more previous meals. For example, instead of generating training data based on carbohydrate information, the one or more processors may generate training data based on glucose sensor data 62 and meal bolus data for the one or more previous meals. As an example, glucose sensor data 62 and the meal bolus data may be provided to a physiological model of patient 12 to back-calculate the amounts of glucose absorbed into the bloodstream of patient 12 over a duration of time due to consumption of the one or more previous meals. Statistical averaging, pattern matching, and/or machine learning techniques may be applied to the training data to determine the correlation, which can be applied to contextual information of future meals to predict amounts of glucose to be absorbed into the bloodstream.

The one or more processors may determine one or more amounts of insulin to counteract effects of the predicted amounts of glucose (86). The effects of the predicted amounts of glucose may be an increase in the glucose level of patient 12. To counteract this increase, one or more amounts of insulin may be delivered to patient 12 to maintain the glucose level within a predetermined range. The one or more amounts of insulin may be determined in a variety of ways. In some examples, the one or more processors may obtain an insulin sensitivity factor for patient 12 (e.g., by retrieving a value stored in memory) and determine the one or more amounts of insulin based on the insulin sensitivity factor. For example, the insulin sensitivity factor may be provided to a mathematical model to predict a glycemic response of patient 12 based on a candidate amount of insulin and the predicted amounts of glucose to be absorbed into the bloodstream over the duration of time. The mathematical model may be used to predict, for each candidate amount of insulin, an amount of time during which a patient's glucose levels remain within a target range, and the candidate amount of insulin that is selected for delivery may correspond to a maximum amount of time within the target range. In some examples, artificial intelligence techniques may be used to determine a dosage of insulin that corresponds to a maximum amount of time within a target range for a patient's glucose levels.

The one or more processors may affect insulin therapy based on outputting information indicative of the determined one or more amounts of insulin (88). For example, to affect the insulin therapy, the one or more processors may communicate, towards an insulin delivery device, the information indicative of the determined one or more amounts of insulin. As one example, the one or more processors may output a control signal to cause the insulin delivery device to deliver particular amounts of insulin. In one example, the insulin delivery device is injection device 30 configured to automatically set an insulin level based on the information indicative of the determined one or more amounts of insulin. In one example, the insulin delivery device is insulin pump 14 configured to automatically deliver the determined one or more amounts of insulin to the patient based on the information indicative of the determined amounts of insulin and/or information indicative of the times when the insulin delivery device is to deliver the determined one or more amounts of insulin.

Figure 9:
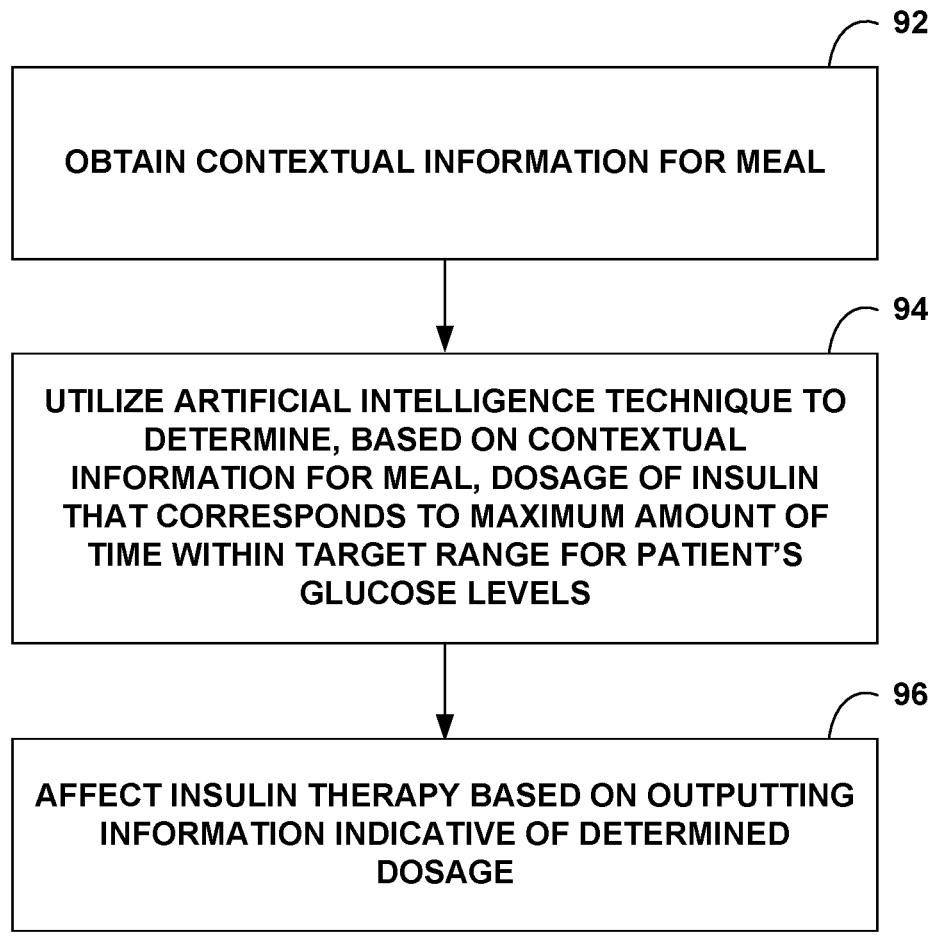
FIG. 9 is a flowchart illustrating an example process for dosage recommendation facilitated by artificial intelligence.

FIG. 9 is a flowchart illustrating an example process for dosage recommendation facilitated by artificial intelligence. The example techniques are described with respect to one or more processors such as one or more processors 28, processing circuitry 32, processing circuitry 40, and/or one or more processors of insulin pump 14.

The one or more processors may be configured to obtain contextual information for a meal (92). Block 92 of FIG. 9 may be similar or identical to block 82 of FIG. 8.

The one or more processors may utilize an artificial intelligence technique to determine, based on the contextual information for the meal, a dosage of insulin that corresponds to a maximum amount of time within a target range for a patient's glucose levels (94). The dosage of insulin may be determined in a variety of ways.

In some examples, the dosage may be determined based on predicting amounts of glucose to be absorbed into a bloodstream of patient 12 over a duration of time. For example, the one or more processors may form an artificial neural network configured to generate a mathematical model for determining the dosage based on genetic programming. The mathematical model may be configured to derive an optimal dosage (e.g., a dosage that maximizes time-in-range) based on the predicted amounts of glucose to be absorbed into the bloodstream.

In some examples, the dosage may be determined using an artificial intelligence technique similar to that discussed above with respect to block 86 of FIG. 8. For example, the one or more processors may generate training data that includes optimal dosages that have been back-calculated for previous meals. Based on the training data, the one or more processors may determine a correlation between contextual information (and/or the predicted amounts of glucose to be absorbed into the bloodstream) and optimal dosages, thereby enabling optimal dosages to be quickly recommended for similar meals in the future.

The one or more processors may affect insulin therapy based on outputting information indicative of the determined dosage (96). For example, to affect the insulin therapy, the one or more processors may communicate, towards an insulin delivery device, the information indicative of the determined dosage. As one example, the one or more processors may output a control signal to cause the insulin delivery device to deliver particular amounts of insulin. In one example, the insulin delivery device is injection device 30 configured to automatically set an insulin level based on the information indicative of the determined dosage. In one example, the insulin delivery device is insulin pump 14 configured to automatically deliver the determined dosage to the patient based on the information indicative of the determined dosage.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media or processor-readable storage media may include computer-readable storage media or processor-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for glucose level management without carbohydrate counting, the system comprising:
one or more processors; and
one or more processor-readable storage media storing instructions which, when executed by the one or more processors, cause performance of:
obtaining contextual information for a meal;
predicting amounts of glucose to be absorbed into a bloodstream of a patient over a duration of time due to consumption of the meal based at least in part on a correlation between the contextual information for the meal and amounts of glucose absorbed into the bloodstream due to the consumption of the meal;
determining one or more amounts of insulin to counteract effects of the predicted amounts of glucose; and
affecting insulin therapy based on outputting information indicative of the determined one or more amounts of insulin.

2. The system of claim 1, wherein the amounts of glucose to be absorbed into the bloodstream comprises a first amount of glucose to be absorbed into the bloodstream at a first time instance within the duration of time, and a second amount of glucose to be absorbed into the bloodstream at a second time instance within the duration of time.

3. The system of claim 1, wherein the one or more processor-readable storage media further store instructions which, when executed by the one or more processors, cause performance of:
prior to predicting the amounts of glucose to be absorbed into the bloodstream, determining a second correlation between contextual information for one or more previous meals and amounts of glucose absorbed into the bloodstream of the patient over a duration of time due to consumption of the one or more previous meals, wherein determining the second correlation is performed without information from the patient relating to carbohydrates consumed from the one or more previous meals.

4. The system of claim 1, wherein determining the one or more amounts of insulin comprises:
obtaining an insulin sensitivity factor for the patient; and
determining the one or more amounts of insulin to counteract effects of the predicted amounts of glucose based on the insulin sensitivity factor.

5. The system of claim 1, wherein determining the one or more amounts of insulin comprises utilizing a mathematical model to predict a glycemic response of the patient based on a candidate amount of insulin and the predicted amounts of glucose to be absorbed into the bloodstream over the duration of time.

6. The system of claim 1, wherein determining the one or more amounts of insulin comprises using an artificial intelligence technique to determine a dosage of insulin that corresponds to a maximum amount of time within a target range for the patient's glucose levels.

7. The system of claim 1, wherein predicting the amounts of glucose to be absorbed comprises utilizing one or more of a group comprising a statistical averaging technique, a pattern matching technique, and a machine learning technique.

8. The system of claim 1, wherein the contextual information comprises one or more of a group comprising a time of day, a day of week, and a patient location.

9. The system of claim 1, wherein affecting the insulin therapy comprises:
communicating towards an insulin delivery device the information indicative of the determined one or more amounts of insulin.

10. The system of claim 9, wherein the insulin delivery device is an injection device configured to automatically set an insulin level based on the information indicative of the determined one or more amounts of insulin.

11. The system of claim 9, wherein the insulin delivery device is an insulin pump configured to automatically deliver the determined one or more amounts of insulin to the patient.

12. The system of claim 1, wherein the one or more processors are included in one or more network devices.

13. A processor-implemented method for glucose level management without carbohydrate counting, the method comprising:
obtaining contextual information for a meal;
predicting amounts of glucose to be absorbed into a bloodstream of a patient over a duration of time due to consumption of the meal based at least in part on a correlation between the contextual information for the meal and amounts of glucose absorbed into the bloodstream due to the consumption of the meal;
determining one or more amounts of insulin to counteract effects of the predicted amounts of glucose; and
affecting insulin therapy based on outputting information indicative of the determined one or more amounts of insulin.

14. The method of claim 13, wherein the amounts of glucose to be absorbed into the bloodstream comprises a first amount of glucose to be absorbed into the bloodstream at a first time instance within the duration of time, and a second amount of glucose to be absorbed into the bloodstream at a second time instance within the duration of time.

15. The method of claim 13, further comprising prior to predicting the amounts of glucose to be absorbed into the bloodstream, determining a second correlation between contextual information for one or more previous meals and amounts of glucose absorbed into the bloodstream of the patient over a duration of time due to consumption of the one or more previous meals, wherein determining the second correlation is performed without information from the patient relating to carbohydrates consumed from the one or more previous meals.

16. The method of claim 13, wherein determining the one or more amounts of insulin comprises:
obtaining an insulin sensitivity factor for the patient; and
determining the one or more amounts of insulin to counteract effects of the predicted amounts of glucose based on the insulin sensitivity factor.

17. The method of claim 13, wherein determining the one or more amounts of insulin comprises utilizing a mathematical model to predict a glycemic response of the patient based on a candidate amount of insulin and the predicted amounts of glucose to be absorbed into the bloodstream over the duration of time.

18. The method of claim 13, wherein predicting the amounts of glucose to be absorbed comprises utilizing one or more of a group comprising a statistical averaging technique, a pattern matching technique, and a machine learning technique.

19. The method of claim 13, wherein affecting the insulin therapy comprises:
communicating towards an insulin delivery device the information indicative of the determined one or more amounts of insulin.

20. One or more non-transitory processor-readable storage media storing instructions which, when executed by one or more processors, cause performance of:
obtaining contextual information for a meal;
predicting amounts of glucose to be absorbed into a bloodstream of a patient over a duration of time due to consumption of the meal based at least in part on a correlation between the contextual information for the meal and amounts of glucose absorbed into the bloodstream due to the consumption of the meal;
determining one or more amounts of insulin to counteract effects of the predicted amounts of glucose; and
affecting insulin therapy based on outputting information indicative of the determined one or more amounts of insulin.

* * * * *